United States Patent [19]
Klausner et al.

[11] Patent Number: 6,122,956
[45] Date of Patent: Sep. 26, 2000

[54] METHOD AND APPARATUS FOR MONITORING CONCENTRATION OF A SLURRY FLOWING IN A PIPELINE

[75] Inventors: James F. Klausner; Renwei Mei; Feng Fu, all of Gainesville, Fla.

[73] Assignee: University of Florida, Gainesville, Fla.

[21] Appl. No.: 09/149,456

[22] Filed: Sep. 9, 1998

[51] Int. Cl.[7] .................................................. G01N 15/06
[52] U.S. Cl. ...................... 73/61.71; 324/439; 324/449
[58] Field of Search .............................. 73/61.41, 67.71; 324/439, 449, 717

[56] References Cited

U.S. PATENT DOCUMENTS

| | | |
|---|---|---|
| 3,729,987 | 5/1973 | Chao et al. . |
| 3,779,070 | 12/1973 | Cushman et al. . |
| 3,853,984 | 12/1974 | Price et al. . |
| 3,926,050 | 12/1975 | Turner et al. . |
| 4,414,841 | 11/1983 | Porenski, Jr. et al. . |
| 4,726,896 | 2/1988 | Grove et al. . |
| 4,866,385 | 9/1989 | Reichwein . |
| 5,008,906 | 4/1991 | Reichwein . |
| 5,065,416 | 11/1991 | Laurila et al. . |
| 5,130,661 | 7/1992 | Beck et al. ............................. 73/61.41 |
| 5,414,195 | 5/1995 | Peterson et al. . |
| 5,576,617 | 11/1996 | Webb et al. ........................... 73/61.41 |

OTHER PUBLICATIONS

Huang et al, "Tomographic imaging of two–component flow using capacitance sensors," *J. Phys. E: Sci. Instrum.*, vol. 22, pp. 173–177 (1989).

KMW Research Co., Technical Brief, "The K1000 Series Conductance Sensor for Percent Solids Measurement".

Holdich et al, Measurement of slurry solids content by electrical conductivity, *Powder Technology*, vol. 72, pp. 77–87 (1992).

*Primary Examiner*—Daniel S. Larkin
*Attorney, Agent, or Firm*—Miles & Stockbridge; Dennis P. Clarke

[57] ABSTRACT

An on-line sensor for measuring volumetric concentration or percent solids of a slurry flowing in a pipeline includes a section of composite or dielectric pipe connected in the pipeline, with a plurality of sensing electrodes mounted around the periphery of the composite pipe having their inner ends in contact with the slurry flowing therethrough. Preferably the inner ends of the sensor electrodes are flush with the inner pipe wall surface. An electrical signal is applied to a bridge circuit that is connected to successive pairs of sensor electrodes around the periphery of the sensor and the ratios of the local conductivity between adjacent pairs of sensing electrodes to the conductivity between a pair of reference electrodes in contact with the liquid are measured and are used to compute the local slurry concentration between adjacent pairs of sensing electrodes. A computer algorithm is used to average the local slurry concentration and produce an output signal representing the average solids volumetric concentration in the pipeline.

14 Claims, 10 Drawing Sheets

METHOD AND APPARATUS FOR MONITORING CONCENTRATION OF A SLURRY FLOWING IN A PIPELINE

BACKGROUND OF THE INVENTION

1. Field of the Invention

This invention relates generally to the measurement of the concentration of solids in a slurry and, more particularly, to a method of and apparatus for measuring the volumetric concentration or percent solids in a slurry flowing in a large diameter pipeline.

2. Description of the Prior Art

The transportation of particulate solids in a liquid slurry is widely used in many industries, and maintaining the concentration of solids in the slurry within relatively narrow limits is essential to successful and economic operation of such systems. For example, when the concentration of solids becomes too high, excessive precipitation or settling can plug the pipeline, making it necessary to shut down and clean the system. Conversely, the cost of operating the slurry pumps is a major consideration and maintaining the concentration as high as practical while avoiding plugging is desirable for economic operation. It is, therefore, desirable to carefully monitor the concentration of the slurry in order to operate such a system near optimum conditions.

Numerous systems have been proposed and developed for measuring particulate concentration in flowing slurry suspensions. For example, the use of radiation attenuation, ultrasonics, microwave resonance, capacitance, conductance, laser, radar, light scattering and light attenuation have been proposed. However, for high concentration slurries in large pipes which may typically be 20 inches or greater in diameter such as those used in mining operations, some of these proposed systems are inoperable or impractical. For example, in such large pipes, light techniques are not usable since the slurry is essentially opaque to radiation in the visible spectrum. Also intrusive sensors are generally considered impractical since the abrasive nature of the slurry quickly erodes and destroys the sensor. As a result, radiation attenuation techniques using gamma rays or x-rays are frequently used, but they may present a radiation hazard to workers and, therefore, the monitors generally must be placed at a location not easily accessible to operating personnel.

A device for measuring the concentration of the slurry moving in a pipeline, using gamma radiation detection techniques, is disclosed in U.S. Pat. No. 5,008,906. This patent generally discusses the configuration and operation of such devices, but does not address the problem of radiation generally associated therewith. Slurry concentration measuring or monitoring devices such as those discussed in this patent are widely used, for example, in phosphate mining operations in which slurry pipelines are used to transport raw materials to the processing plant. The practice generally has been to locate the gamma ray densitometer near the end of the pipeline or in the processing plant in a remote location not routinely accessible to mine operators. In such an installation, the water jet operator who continuously mixes the slurry does not know the slurry concentration until it reaches the densitometer which may involve a delay time of up to an hour or more. Thus, since the gamma ray densitometer readout does not provide an instantaneous indication of the concentration of the slurry being mixed, it is conventional practice to rely upon the jet operator's experience and the pump motor amperage as an instantaneous indicator of slurry concentration at the pump discharge. This practice can lead to costly shut-downs due to plugging or to inefficiencies due to low concentration.

The measurement of slurry solids content by electrical conductivity is discussed by Holdridge et al in an article entitled "Measurement of Slurry Solids Content by Electrical Conductivity" published in 72 Power Technology at pages 77–87 (1992). Their tests evaluated sedimentation and flowing slurries of various solids in a conducting fluid, i.e., water, utilizing electrical conductivity of the slurry as an indication of solids concentration. In these tests, a pair of electrodes were mounted in diametrically opposed relation to one another to measure the conductivity of the slurry across the full diameter of the stream. It was stated that electrode design and positioning is critical and that electrodes mounted flush with the wall of the container vessel interfere with electrical field flux and give rise to poor reproducibility of results from calibrations. Difficulties in generating an attenuating signal which can pass through a large diameter pipe containing a high concentration slurry was not addressed.

It is known that the concentration of solids in a slurry moving in a pipeline is not always uniform throughout the cross-section of the pipe. For example, in horizontal pipes with solids having specific gravity greater than one, and particularly in long horizontal runs of pipe, a stratification of solids will develop from the top to the bottom of the pipe, with a minimum of solids at the top and a maximum concentration near the bottom.

It is also known that the conductivity of the conveying fluid may vary in a commercial slurry transport system such as used in a phosphate mining and processing plant. For example, in a water slurry of phosphate matrix, the amount of soluble chemicals in the matrix may vary substantially, with the result that ionization and consequently the conductivity of the fluid will not always remain constant even though the composition of the water used to mix the slurry is unchanged. Thus, in a concentration sensor utilizing conductivity as a measure of concentration, variations in conductivity of the liquid phase of the slurry will adversely affect the reliability of the indicated concentration. It is, accordingly, a primary object of the present invention to provide an improved on-line sensor for sensing and indicating the concentration or percent of solids moving in a large slurry pipeline.

Another object is to provide an improved method of and apparatus for providing an accurate and instantaneous indication of the slurry concentration at or adjacent the entrance to the pipeline, and for providing a feedback for controlling the solids in the slurry to near the optimum concentration.

An additional object is to provide a method of and apparatus for measuring a slurry concentration, utilizing the conductivity of the slurry as an instantaneous indicator of concentration.

A further object is to provide such a slurry concentration measurement system utilizing a plurality of sensing electrodes spaced around the pipeline in an annular array for measuring the conductivity of the slurry.

Yet another object is to provide such a system which is not affected by erosion resulting from the abrasive slurry moving through the pipeline.

A still further object is to provide such a system including means for continuously monitoring the conductivity of the liquid phase of the slurry, and for adjusting the calibration of the system to compensate for variations in the liquid conductivity.

It is another object to provide a slurry concentration sensor which will provide an average volumetric percent solids measurement of the slurry, and provide an instantaneous readout or display of the concentration measurement which may be utilized to control the mixing system and thereby the solids concentration entering the pipeline.

SUMMARY OF THE INVENTION

In the attainment of the foregoing and other objects and advantages, an important feature of the invention resides in providing a slurry concentration sensor utilizing the conductivity of the slurry as an indication of slurry solids, and employing a plurality of electrodes arranged in equally spaced relation around the periphery of the pipeline to measure conductivity. The conductivity measured between adjacent electrodes relative to the conductivity measured for the conveying liquid is related to the local slurry concentration flowing between the two electrodes. Measurement of the conductance between each pair of adjacent electrodes around the pipeline provides local concentration data, and a computer algorithm is employed to translate local concentration data to an average volumetric percent solids measurement. Non-intrusive sensors or electrodes are employed to minimize erosion and the resultant calibration drift or changes and, in a preferred embodiment, the system is employed in a horizontal section of pipe to minimize effects of turbulent flow.

The sensor preferably comprises a length of composite pipe formed of a dielectric material, with the individual electrodes mounted in the composite pipe wall and each having its inner end flush with the inner pipe surface. A computer controlled analog-to-digital system and signal generator is employed to measure conductance through the sensor array. The sensor electrodes are connected in the system via solid state switching relay and bridge circuitry. The computer system controls the circuits and implements the computational algorithm required to make the measurements. The computer display may provide a graphical output of the instantaneous local and average percent solids, and the output may be utilized through suitable controls to automatically control the slurry jets and/or pumps and thereby the concentration of solids entering the pipeline.

In the preferred embodiment, a pair of reference electrodes are located in axially spaced relation to one another at the top of the horizontal pipe to measure the conductance of the liquid phase of the slurry. While some minimal amount of solids may be present in the slurry at this location, the system may be calibrated to effectively eliminate the influence of the minimum solids present, and a signal representing the conductance measured between the reference electrodes is supplied to the computer and employed in calculating the percent solids in the slurry.

Other arrangements may be employed to continuously monitor the liquid phase conductivity when the system is installed in a turbulent, or other than horizontal, section of pipe. For example, a portion of the slurry flowing through the pipeline in the vicinity of the sensor may be diverted and caused to flow past a porous filter that can block the solids and the remaining liquid flows through a horizontal pipe section where normal solids stratification can occur, with the reference electrodes being located in this horizontal pipe. Alternatively, the reference electrodes may be located in a settlement chamber, and a portion of the slurry may be diverted into the chamber and allowed to settle. The settlement chamber can then be drained or flushed back into the main pipeline and this procedure repeated.

BRIEF DESCRIPTION OF THE DRAWINGS

Other features and advantages of the invention will be apparent from the detailed description contained hereinbelow, taken in conjunction with the drawings, in which.

DESCRIPTION OF THE PREFERRED EMBODIMENTS

Figure 1:
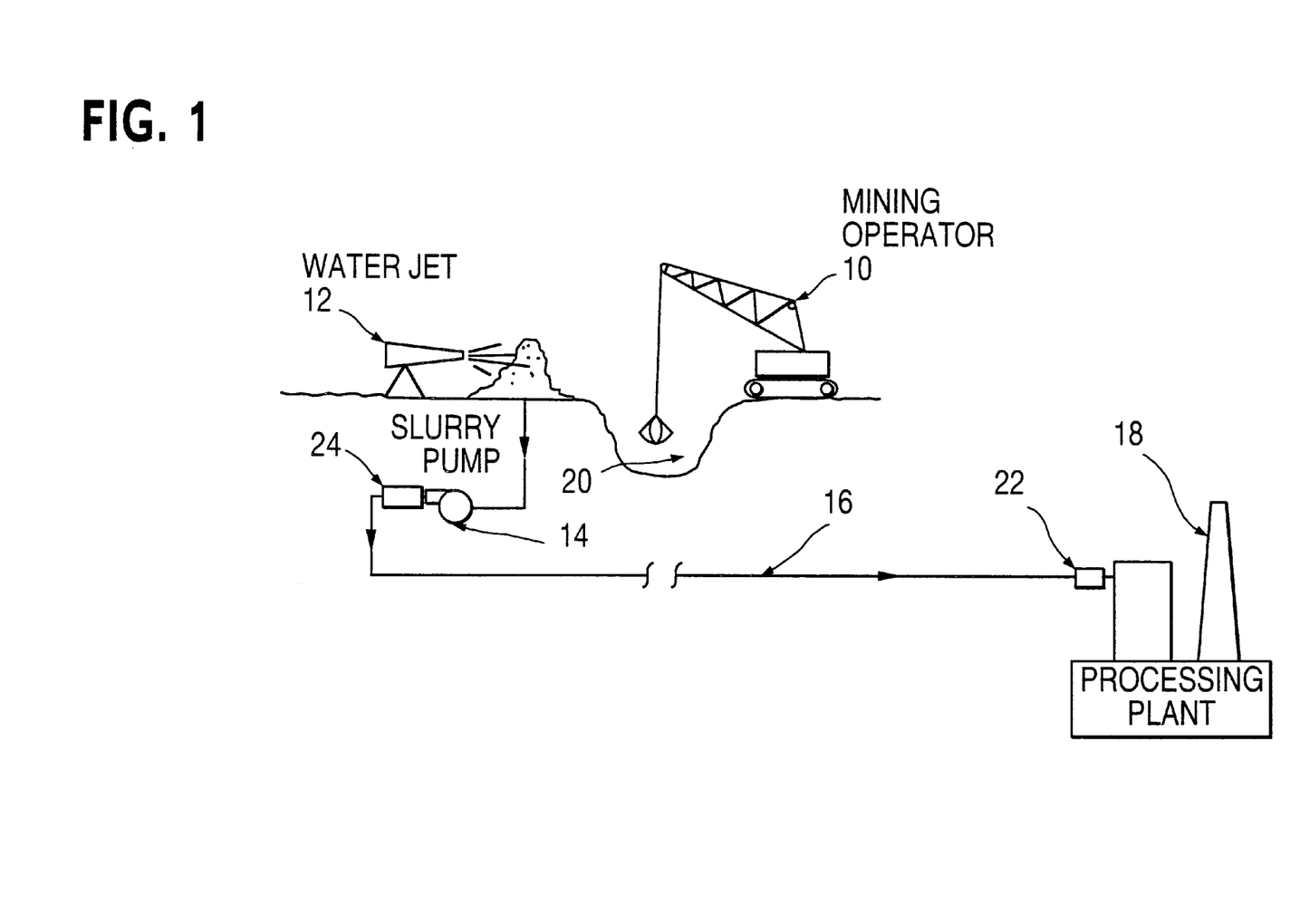
FIG. 1 is a diagrammatic view schematically illustrating a slurry pipeline system utilized in a mining and processing installation.

Referring now to the drawings in detail, FIG. 1 illustrates an open pit mining and processing installation in which the mine matrix is lifted from the open pit by suitable means such as a clam shell or drag line bucket supported and operated by a crane indicated generally at 10, with the matrix being deposited at a jetting platform where an operator controls a water jet system indicated schematically at 12 to wash or jet the matrix to the inlet of a slurry pump 14 which pumps the slurry through a large diameter pipeline 16 to a processing plant 18 located a substantial distance from the open pit 20.

In the typical commercial phosphate mining operation, the concentration of solids in the water-solids slurry flowing in pipeline 16 is continuously monitored by a gamma ray densitometer 22. Because of the radiation hazard to personnel, gamma ray densitometers are typically located in the processing plant at a location not readily accessible to operating personnel. Since the processing plant 18 is typically located a substantial distance from the open pit 20, it normally requires from several minutes to an hour or more for the slurry to flow from pump 14 to the densitometer 22. Thus, while gamma ray densitometers are capable of providing a reliable indication of the concentration of solid particles in a slurry moving through pipeline 16, this is of little value to the operators controlling the mixing jets 12 and pump 14 where the concentration of solids entering the pipeline is of primary concern. Thus, in accordance with the present invention, a conductance-type densitometer, or concentration sensor 24, which does not present a hazard to personnel, is installed downstream of and closely adjacent to the pump 14.

Figure 4:
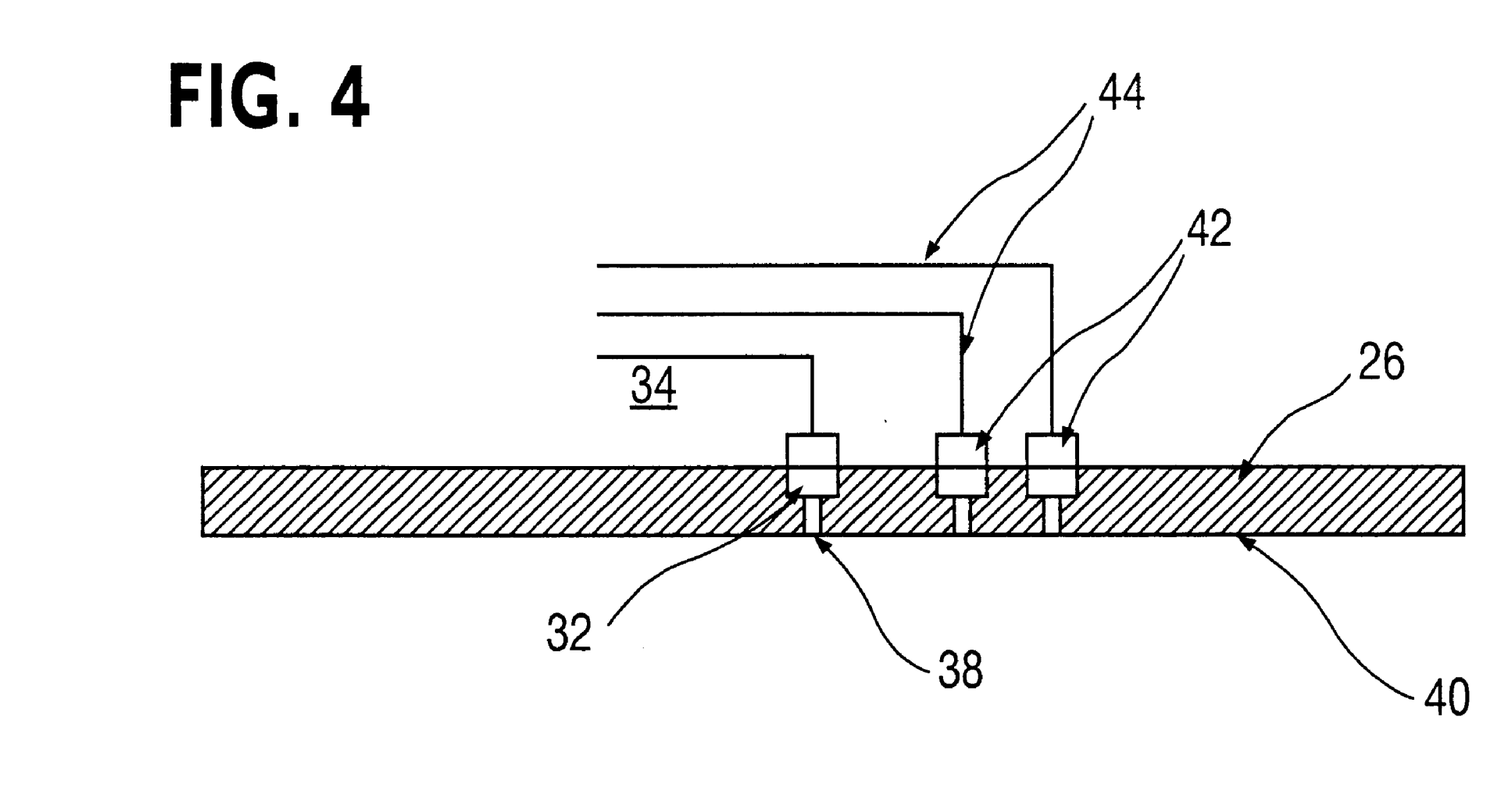
FIG. 4 is a fragmentary sectional view taken along line 4—4 of FIG. 3.

Referring now to FIGS. 2–5, it is seen that the sensor 24 includes a sensor body in the form of a length of pipe 26, preferably with flanges 28, 30 formed one on each end thereof for connecting the pipe body in the pipeline 16. The pipe body 26 is formed from a composite dielectric material having sufficient strength and durability to withstand the pressure and abrasion of the slurry flowing through the pipeline. A plurality of conductor sensing electrodes 32 are mounted in equally spaced relation to one another in an annular array around the central portion of pipe 26, and each electrode 32 is connected through a conductor 34 to a switching relay circuit 36 as shown schematically in FIG. 5. As shown in FIG. 4, each electrode 32 extends through the wall of pipe 26 and has its inner end 38 flush with the inner surface 40 of pipe 26. The number of electrodes 32 in the annular array will depend upon the diameter of the pipe 26 as well as on the accuracy, or resolution, of the measurement to be taken. In a prototype sensor, thirty-six electrodes were installed in a Garolite G11 (phenolic resin composite) pipe having a six-inch inside diameter, and test results using this experimental arrangement were very successful.

Figure 2:
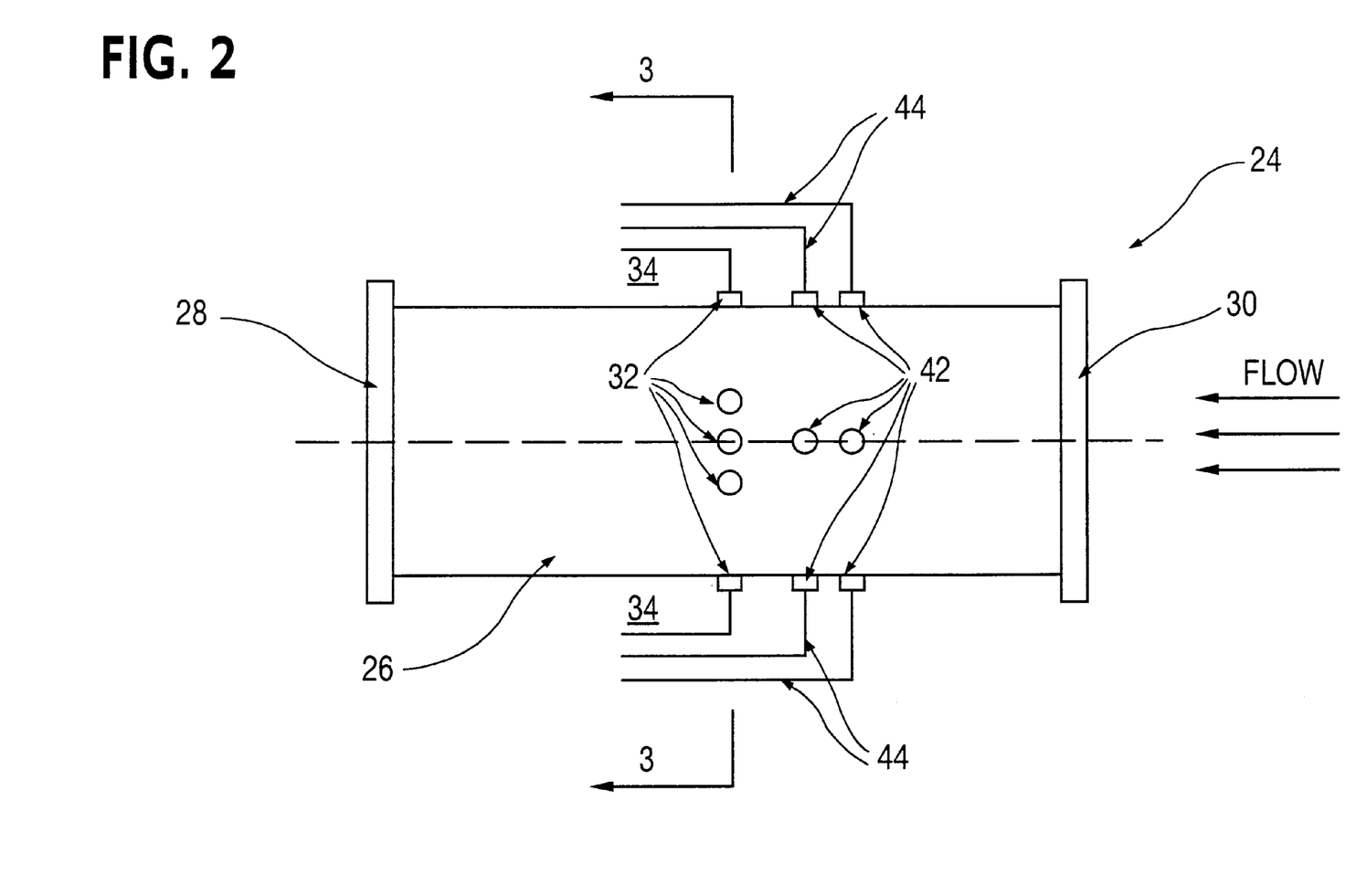
FIG. 2 is an elevation view schematically showing conductance electrodes mounted in a segment of pipe for insertion in a slurry pipeline.
Figure 3:
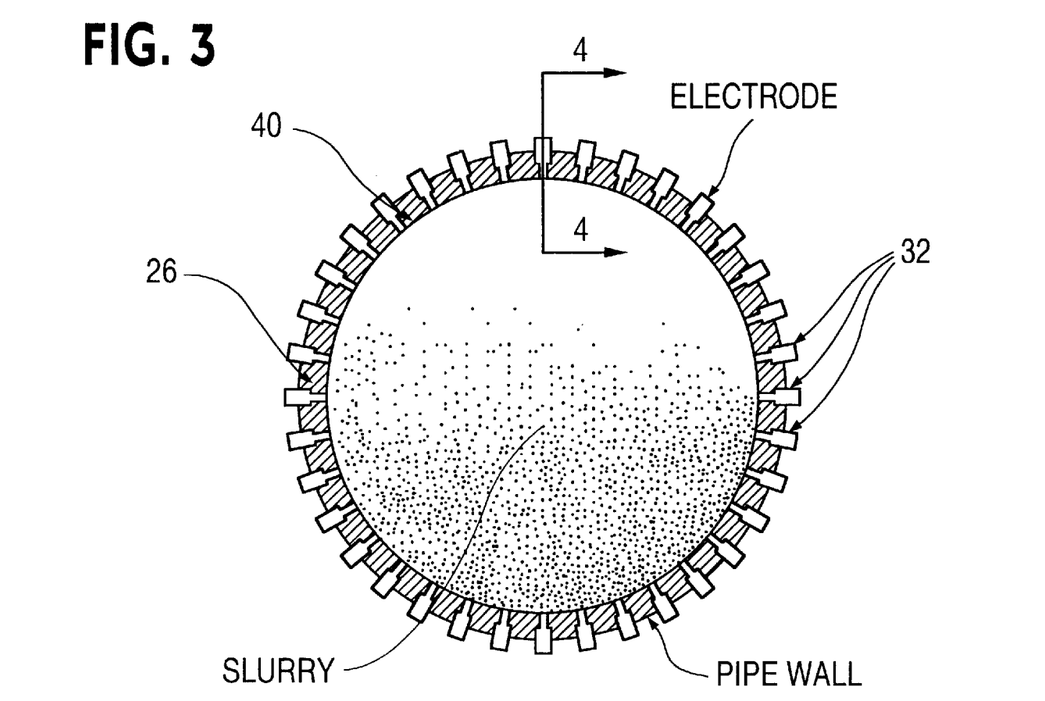
FIG. 3 is an enlarged sectional view taken along line 3—3 of FIG. 2.

A pair of reference electrodes 42 are also mounted in the wall of pipe 26, in axially spaced relation to one another at the top of the pipe 26, as installed in a horizontal run of pipeline 16. Reference electrodes 42, 42 are connected in the bridge circuitry 39 by conductors 44, and are used to measure the conductivity of the liquid phase of the slurry, assuming that, due to gravitational stratification, the liquid at the top center of the pipe is substantially pure liquid. It is recognized, of course, that there will be some particles entrained in the liquid at the top of the pipe 26 despite such gravitational stratification, but the number of particles in this area is typically very low and any variation in the number of particles has been shown to be sufficiently low (for solids with specific gravity greater than two) as to cause negligible error in a working sensor and can readily be compensated for in calibrating the sensor.

For reasons pointed out hereinbelow, it is desirable to provide a plurality of pairs of sensor electrodes 32 at spaced positions around the periphery of the pipe, for example, at 90° intervals, but only one pair, i.e., the top pair, is connected in the circuitry during operation.

As previously stated, it has long been recognized that the conductivity of a slurry varies with the concentration of solid particles in the slurry. In the sensor configuration described above, the conductivity ratio K measured between any adjacent pair of electrodes relative to the conductivity for the pure liquid thus bears a relation to the slurry concentration flowing between the respective pairs of electrodes. It has been shown that the solids concentration C, by volume fraction, may be expressed as:

$$K = \frac{1-C}{1+0.5C}$$

where $$K = k_m \div k_l$$

and $k_m$ is the mixture conductivity and $k_l$ is the liquid conductivity, assuming that the solids are non-conducting. Conductivity sensors typically require calibration, and C is normally expressed as $C=1-K^{1/n}$.

Relying upon the above relation, an experimental conductivity sensor was constructed and tested. The system included a mixing container for supplying a slurry of known solids concentration to a pump which circulated the slurry through the sensor installed in a horizontal section of pipe and then returned to the mixing container. An electric circuit designed to measure the slurry-to-liquid conductivity ratio was connected to the sensor electrodes. One axially spaced pair of electrodes at the top of the conduit were used to measure the conductivity of the liquid phase while a second pair of sensor electrodes located one at the top and one at the bottom of the pipe were connected in a Wheatstone bridge circuit. The conductivity ratio K, as measured by the circuitry, may be expressed as:

$$K = \frac{k_m}{k_l} = \left\{ \frac{A_l}{A_m} \frac{d_m}{d_l} \right\} \frac{R_l}{R_m}$$

where A is the electrode surface area exposed to the slurry, d is the distance between electrodes, R is the resistance across the respective electrode pair, m refers to the mixture and l refers to the liquid phase. Thus, using the Wheatstone bridge theory, it may be shown that:

$$K = \text{constant} \left( \frac{V_r}{V_2} - 1 \right) \bigg/ \left( \frac{V_r}{V_1} - 1 \right)$$

where $V_1$ and $V_2$ are the measured bridge arm voltages and $V_r$ is the reference input voltage supplied by a function generator.

Figure 6:
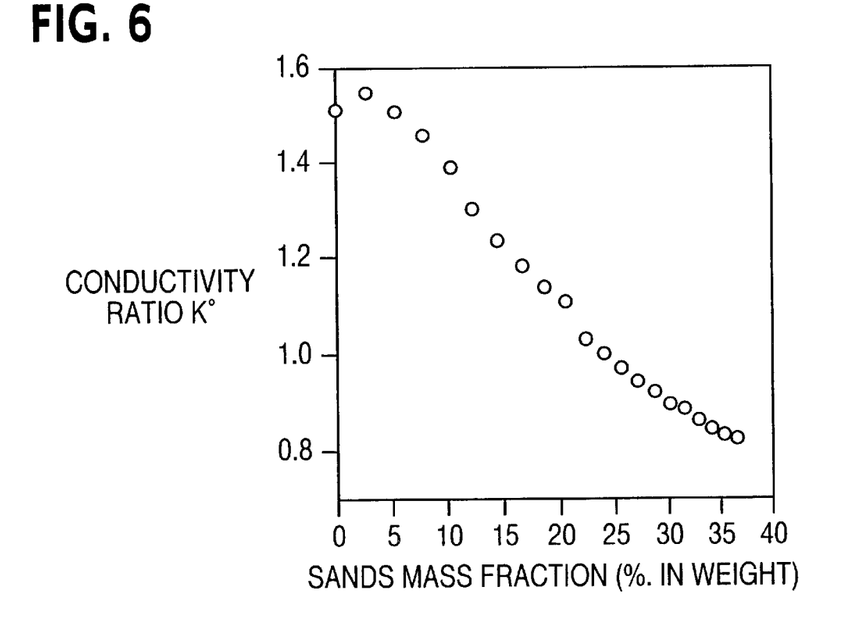
FIG. 6 is a plot of the measured conductivity ratio between the fluid phase and the slurry, using sand as the slurry solid, for various fraction of solids.

Experiments using the pilot facility were initially completed using sand as the slurry solid and water as the liquid. FIG. 6 shows a plot of the measured sand slurry concentration flowing through the sensor as a function of K' when K'=K/calibration constant. FIG. 6 shows that the sensor response is excellent with little scatter in the data.

Figure 7:
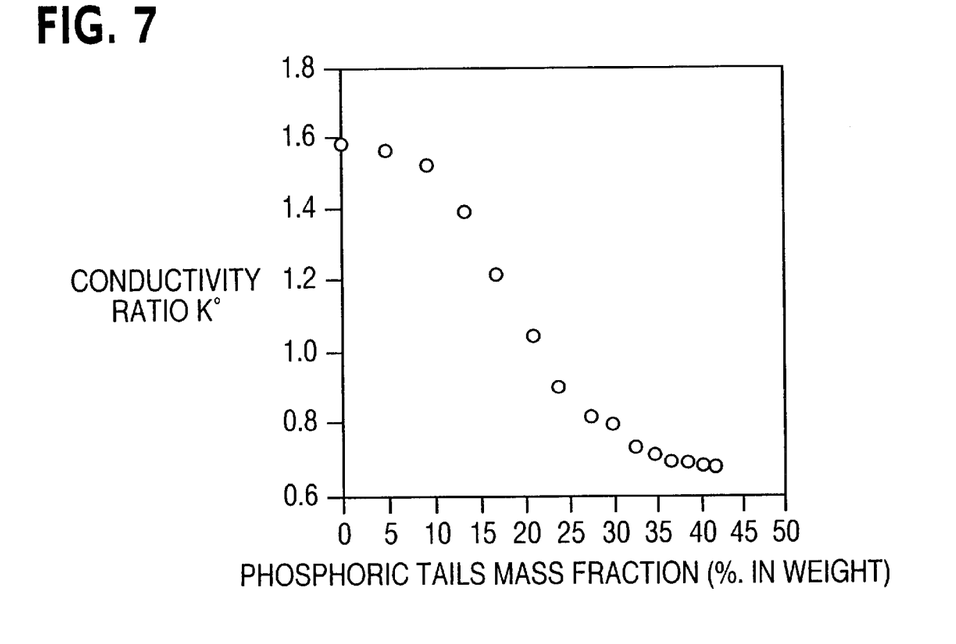
FIG. 7 is a view similar to FIG. 6, using phosphoric tails as the solids.

Subsequent tests were completed using phosphoric tails as the slurry solids and the results of these tests are illustrated in FIG. 7. Again excellent results are obtained. These experimental results demonstrate that conductance may be utilized as a reliable measuring technique for determining slurry concentration flowing in a pipe.

Although the above test results clearly demonstrate that slurry conductance reliably reflects the slurry concentration flowing in a small diameter pipe, the variables which may be encountered in a large pipe of, for example, 20 inches or more in diameter which may be encountered in a commercial slurry transportation system could render a single pair electrode sensor unreliable. This is overcome in accordance with the present invention wherein a large number of electrodes 32 are arranged around the periphery of the dielectric pipe section 26, and conductance is measured between adjacent pairs of electrodes and utilized to provide local concentration data.

Figure 5:
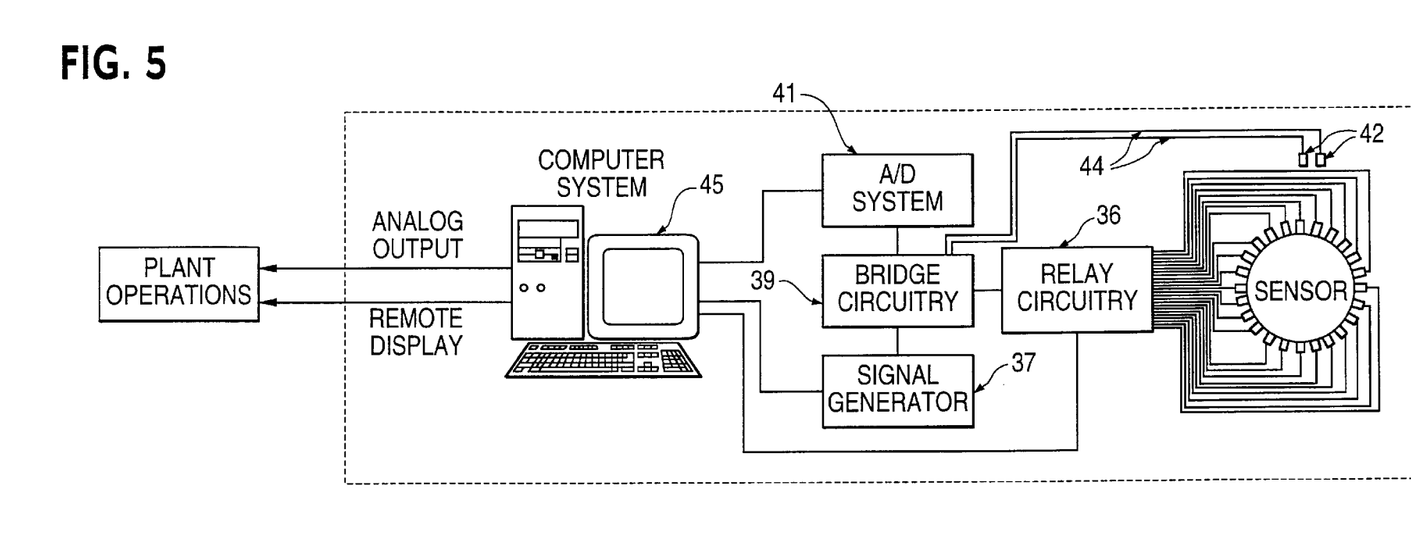
FIG. 5 is a block diagram illustration of the sensor circuitry according to the present invention.

As shown in FIG. 5, each of the sensor electrodes 32 is connected through the high speed switching relay circuit 36 to a signal generator 37 and a bridge circuit 39. A single set of reference electrodes 42 located at the top of pipe 26 is also connected to the bridge circuit 39 through conductors 44. The high speed solid state relay circuitry 36 switches between adjacent pairs of sensor electrodes 32, which are connected in bridge circuit 39 in rapid succession, and the bridge circuitry is connected through an analog-to-digital converter 41 to a computer 45 where an algorithm translates the sensor measured data to a local volume percent of solids measurement between adjacent electrodes. The percent solids by volume is related to the percent solids by mass through:

$$X = \frac{1}{1 + 1/SG(1/C - 1)}$$

where X is the percent solids by mass and SG is the specific gravity of the solids.

Therefore, the computer algorithm can easily provide the percent solids on a mass basis or volumetric basis. It is typical that industrial users prefer the percent solids on a mass basis.

Figure 9:
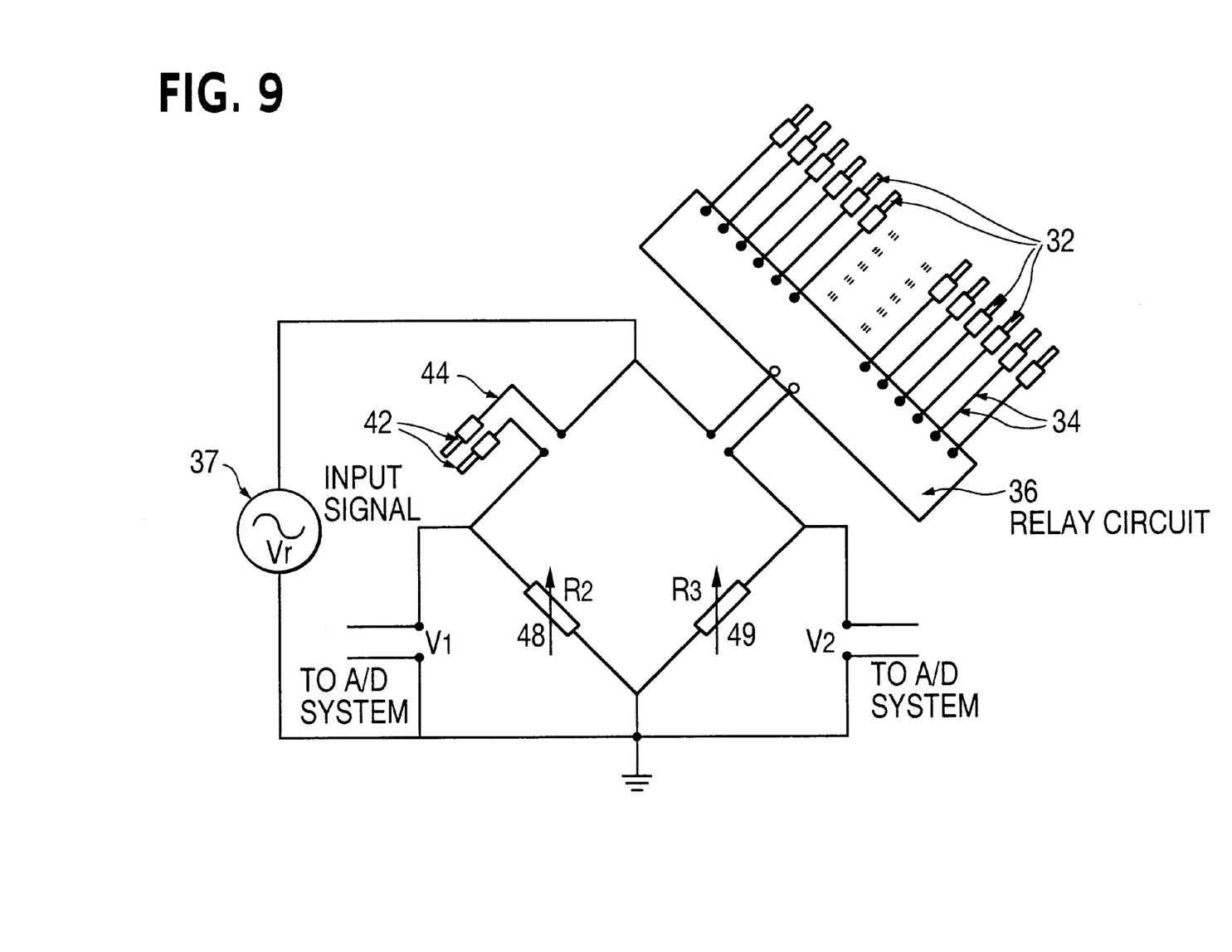
FIG. 9 shows the bridge circuit used for measuring the conductivity ratio.

FIG. 9 shows a typical bridge circuit 39. The arms of the circuit are comprised of reference electrodes 42, sensor electrodes 32 connected through a relay circuit and variable resistors 48 and 49. Typically, the variable resistors are adjusted to have the same resistance of approximately 10,000 ohms. A computer-controlled signal generator 37 supplies the bridge circuit 39 with an input signal. The ratio of the slurry mixture conductivity flowing past the sensor electrodes 32 to the liquid conductivity flowing past the reference electrodes 42 is computed from:

$$K = \text{constant} \left(\frac{V_r}{V_2} - 1\right) \bigg/ \left(\frac{V_r}{V_1} - 1\right)$$

where $V_r$ is the input signal voltage, $V_1$ and $V_2$ are the measured bridge arm voltages shown in FIG. 9. Once K is determined for a sensor electrode pair, the local slurry concentration across the electrode pair is computed from $C=1-K^{1/n}$, where n must be determined from calibration.

Figure 10:
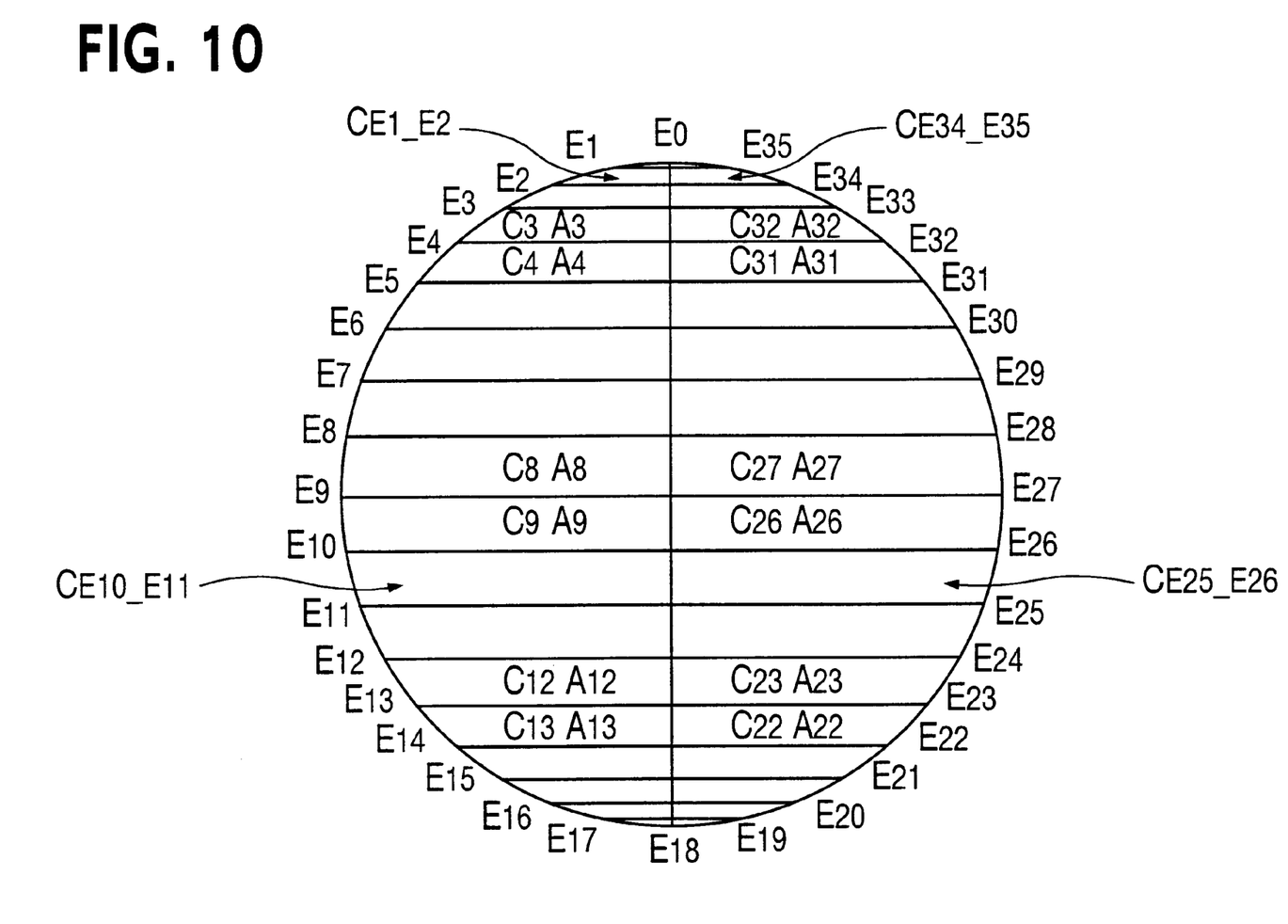
FIG. 10 is a pictorial of the electrode arrangement and sensor cross-section that is used to explain the measurement algorithm.

The preceding description explains the manner in which the local concentration between adjacent electrodes is determined. The local concentration information in itself is valuable information and may be pictorially displayed on a computer monitor, printed out in graphical form, saved on a storage medium in digital format or transmitted to a digital processor for further analysis, depending on the application. However, in an industrial setting, operating personnel and control processors are most interested in the average solids concentration. In order to explain the manner in which the average solids concentration is determined, consider FIG. 10 which shows a cross-section of the concentration sensor. A sensor with thirty-six electrodes, numbered as $E_0$–$E_{35}$, is described. The sensor is sectioned into areas where $A_3$ denotes the area occupying half of the sensor between electrodes $E_3$ and $E_4$, and $A_{32}$ denotes the area occupying half of the sensor between electrodes $E_{32}$ and $E_{33}$. $C_3$ denotes the local volumetric concentration measured between electrodes $E_{32}$ and $E_{33}$. Once the procedure for measuring the local concentrations, $C_0$, $C_1$, $C_2$, . . . $C_{33}$, $C_{34}$, $C_{35}$, has been implemented, the mean value theorem is used to compute the average concentration in the sensor:

$$\overline{C} = \frac{1}{A}\int_A C(A)dA = \frac{1}{A}\sum_{i=0}^{35} C_i A_i$$

where $\overline{C}$ is average percent solids concentration by volume, A is the cross-sectional area of the sensor, $C_i$ is the local concentration measured by the electrode pair i under consideration as described above, and $A_i$ is the sectional area of the sensor to which the local concentration $C_i$ corresponds.

As previously indicated, in a substantially horizontal section of the slurry pipeline, gravitational stratification will inherently occur, with the heaviest concentration of solids near the bottom of the cylindrical pipe and the least concentration at the top. It is assumed that the solids concentration in any horizontal plane will be substantially uniform, but any variation in such uniform stratification is compensated for by the use of a large number of sensing electrodes spaced around the periphery of the pipe and by rapid switching between adjacent pairs of sensing electrodes to provide a real time output.

Figure 11:
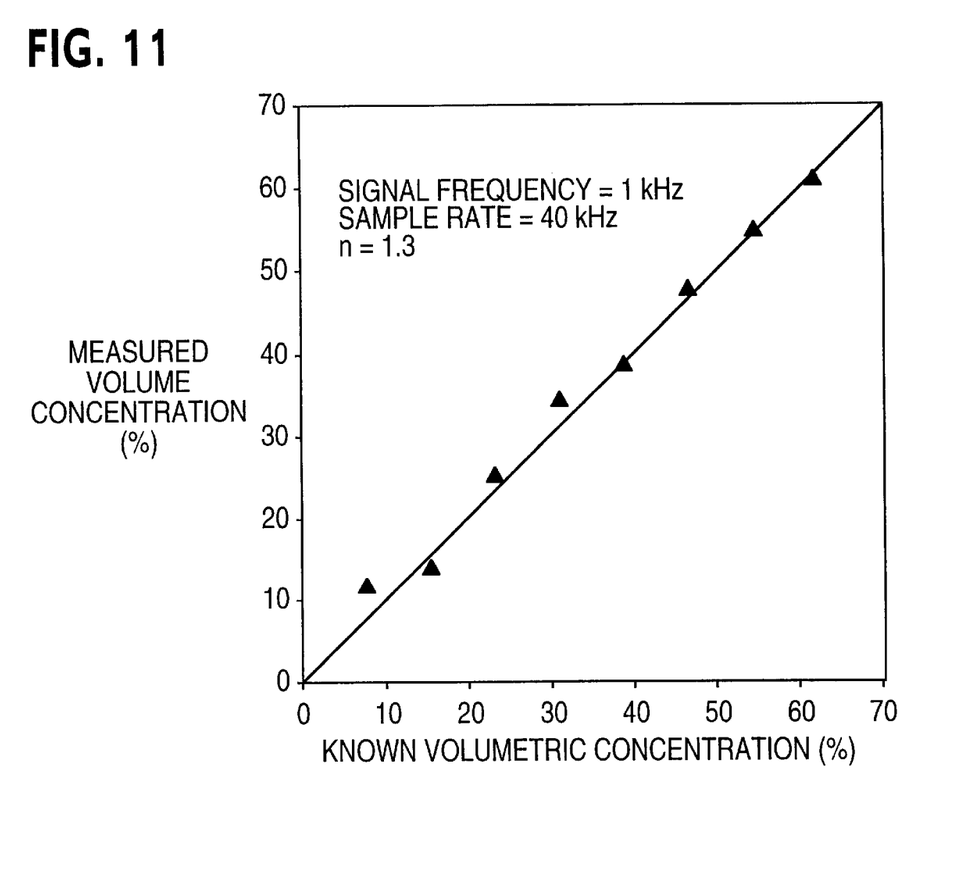
FIG. 11 shows a typical calibration for the sensor using a sand slurry.

As mentioned earlier, a six-inch inside diameter prototype sensor was fabricated from Garolite G11 which used thirty-six electrodes 32 equally spaced around the periphery of the sensor body 26. Two reference electrodes 42 were mounted at the top of the pipe as shown in FIGS. 2 and 4. The sensor was installed in a slurry transport pipeline mounted in the horizontal configuration. FIG. 11 shows the measured average volumetric concentration of sand particles versus the known volumetric concentration. It is seen that the agreement is very good. In the relation $C=1-K^{1/n}$, a value of 1.3 was used which was determined through this calibration.

Tests conducted on apparatus in which the electrodes projected into the path of the flowing slurry demonstrate that the slurry quickly erodes the surface of the electrodes and that such erosion is not uniform around the periphery of the pipe. Such erosion quickly influenced calibration of the system, and it has now been shown that sensing electrodes having their inner surface flush with the inner surface of the composite pipe section provide more uniform, reliable measurement results. Preferably, once the electrodes 32 and 42 are mounted in pipe 26, their inner ends 38 are ground so as to be flush with the inner surface 40 of the pipe wall.

It has also been shown that heavier concentrations of particles in a slurry in the lower sections of a substantially horizontal pipe results in this lower section being eroded more rapidly by the abrasive solids in the slurry. Accordingly, in order to extend the useful life of the sensor, it is desirable to be able to periodically rotate the sensor to expose different areas of the internal pipe surface to the heavy erosion area. To accomplish this, a plurality of sets of reference electrodes 42 are provided. Preferably, at least four pair of electrodes 42 are arranged in equally spaced relation around the periphery of the composite pipe section. only the electrodes 42 at the top of pipe 26 are connected to the bridge circuit during operation, however, with the remaining three sets acting only as spares to be utilized when the sensor is rotated. This may be desirable, in a highly erosive slurry, at standard maintenance intervals, e.g., every six months, to prolong the life of the system. It has also been determined that the substantially flush ends of the electrodes will erode at substantially the same rate as the pipe wall so that the surface area of the electrodes which is exposed to the slurry remains substantially constant throughout the life of the sensor and recalibration is not required as a result of electrode erosion.

While it has been shown experimentally that a pair of sensor electrodes installed in the top of a substantially horizontal pipe section may be utilized as a reliable indicator of the conductivity of the fluid phase of the slurry, it may be desirable to install the sensor in an other than horizontal pipe section or at a location where substantial turbulence exists. This may be accomplished in an arrangement shown schematically in FIG. 8 where a portion of the flow through the sensor pipe 26 (or an adjacent portion of the pipeline 16 ) is diverted and caused to flow through a horizontal section of auxiliary pipe 50 having the reference electrodes 42 installed in the top portion thereof, with the flow then being returned to the pipeline. In such an arrangement, the length of horizontal pipe 50 would be sufficiently long and/or the flow sufficiently slow to permit gravitational stratification in substantially the same manner as in the embodiment described above so that the reference conductivity measurement would reliably represent the conductivity of the fluid phase flowing through the system on a continuous basis.

Figure 8:
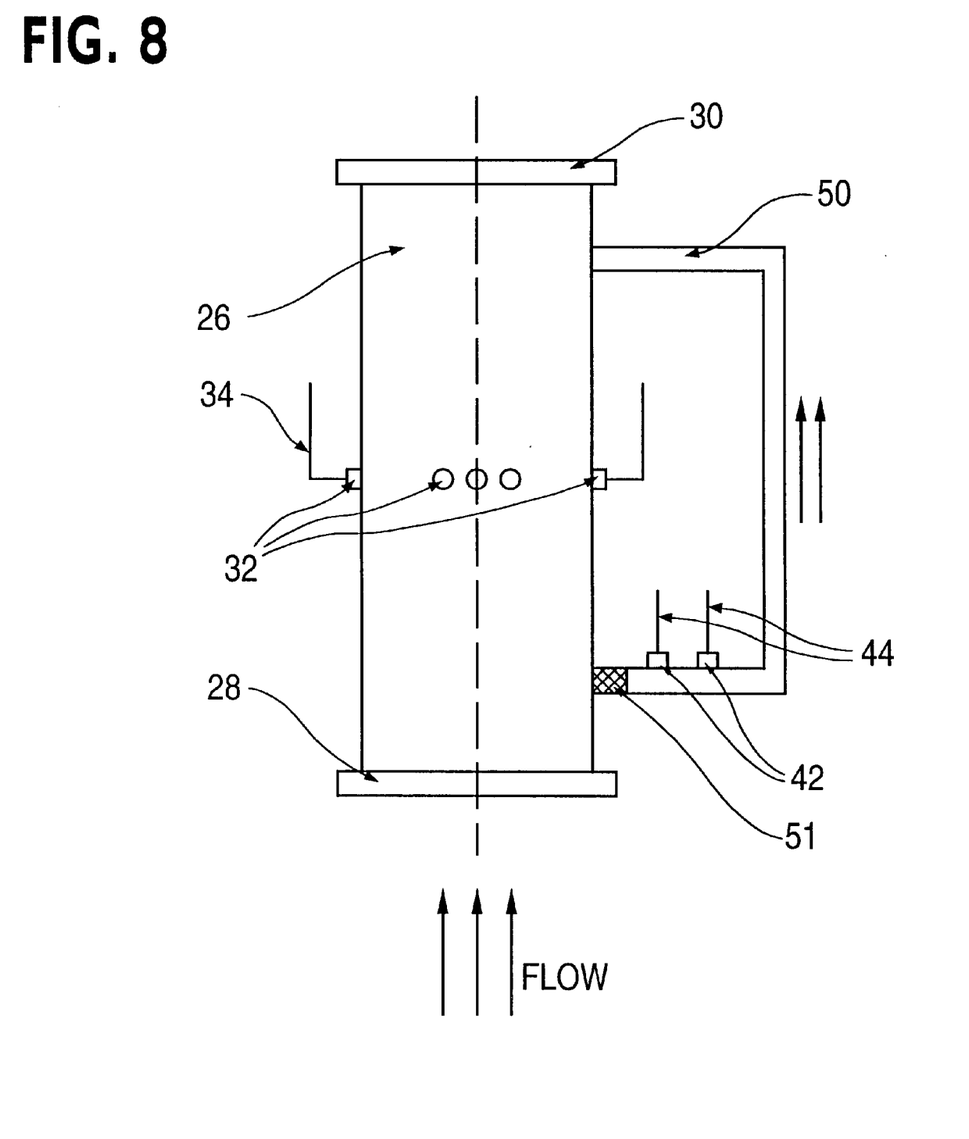
FIG. 8 is a fragmentary schematic showing of an alternate arrangement of the reference electrodes.

It may also be desirable to insert a porous medium 51 at the entrance to the auxiliary line 50 in order to substantially filter out the majority of suspended solids. In this way, the diameter and length of the auxiliary line may be substantially reduced.

In a further modification, a portion of the flow from pipe 26 may be diverted through a sedimentation chamber where the reference electrodes would contact the fluid phase. The sedimentation chamber can be progressively periodically drained. In any event, it is desirable for the reference electrodes to measure the actual conductivity of the liquid phase substantially continuously or at frequent intervals to avoid erroneous concentration measurement readings as a result of any change in liquid phase conductivity during operation.

While preferred embodiments and applications have been disclosed and described, it should be understood that the invention is not so limited, and it is intended to include all embodiments which would be apparent to one skilled in the art and which come within the spirit and scope of the invention.

We claim:

1. A method of monitoring the solids concentration of a liquid-solid slurry flowing in a slurry pipeline comprising the steps of:

providing an annular array of sensor electrodes in a section of the pipeline, said sensor electrodes being equally spaced around the pipeline and having one end extending therethrough into contact with the flowing slurry, applying an electrical signal to each adjacent pair of said sensing electrodes and measuring the conductivity of the slurry between each pair of electrodes in succession around the array, averaging the conductivity measured between each pair of sensor electrodes, providing a pair of spaced reference electrodes in contact with the liquid phase of the slurry, applying an electrical signal to said reference electrodes and measuring the conductivity of the liquid phase of the slurry, and comparing the conductivity measured by said sensor electrodes and the average of the conductivity measured by said pairs of reference electrodes and producing an output signal proportional to the solids content in the slurry.

2. The method defined in claim 1 comprising the step of supplying the conductivity measurements by said reference electrodes and said pairs of sensor electrodes to a computer and utilizing the computer to average the conductivity measurements from the pairs of sensor electrodes and to compare the average conductivity with the reference conductivity measurements to produce an output signal proportional to the solids concentration in the slurry.

3. The method defined in claim 2 further comprising providing a computer controlled circuitry between said computer and said reference and sensor electrodes, the computer controlled circuitry including a signal generator for supplying electrical signals to be applied to the reference electrodes and the sensor electrodes, bridge circuitry for measuring the conductivity, a solid state relay circuit for rapidly connecting the respective sets of sensor electrodes to the signal generator and the bridge circuit, and an analog-to-digital system for supplying the bridge circuit measurements to the computer.

4. The method defined in claim 1 further comprising the step of providing a section of dielectric pipe connected in and forming a part of the slurry pipeline, said annular array of sensor electrodes being mounted in the dielectric pipe section.

5. The method defined in claim 4 comprising the step of supplying the conductivity measurements by said reference electrodes and said pairs of sensor electrodes to a computer and utilizing the computer to average the conductivity measurements from the pairs of sensor electrodes and to compare the average conductivity with the reference conductivity measurements to produce an output signal proportional to the solids concentration of the slurry.

6. The method defined in claim 5 further comprising providing a computer controlled circuitry between said computer and said reference electrodes and said sensor electrodes, the computer controlled circuitry including a signal generator for supplying electrical signals to be applied to the reference electrodes and the sensor electrodes, bridge circuitry for measuring the conductivity, a solid state relay circuit for rapidly connecting the respective sets of sensor electrodes to the signal generator and the bridge circuit, and an analog-to-digital system for supplying the bridge circuit measurements to the computer.

7. The method defined in claim 6 wherein said section of dielectric pipe is connected in a substantially horizontal section of the slurry pipeline, and wherein said reference electrodes are mounted in axially spaced relation substantially at the top of said dielectric pipe.

8. A system for monitoring the concentration of solids in a liquid-solid slurry flowing in a pipeline comprising:

a pipe section formed from a dielectric material connected in and forming a part of the pipeline, a plurality of sensor electrodes mounted on said pipe section and having one end extending through the wall thereof for contact with a slurry flowing therethrough, said sensor electrodes being mounted in an annular array around the periphery of the pipe section in equally spaced relation to one another, a pair of reference electrodes mounted in fixed relation to one another and in contact with the liquid phase of the slurry, means for applying a first electric signal across each adjacent pair of said sensor electrodes in succession around said annular array and for measuring the conductance of the liquid slurry between each said pair of sensor electrodes, means for applying a second electrical signal across said pair of reference electrodes and for measuring the conductance of said liquid phase of the slurry between said pair of reference electrodes, and means for averaging the conductance measurements between said pairs of sensor electrodes and for comparing the average conductance with the conductance measured by said reference electrodes to produce a signal representing the solids concentration in the slurry.

9. The system defined in claim 8 further comprising signal generator means producing said first and said second electrical signals, and switching relay means for applying said first signals to each said adjacent pair of sensor electrodes.

10. The system defined in claim 9 wherein said means for averaging the conductance measurements comprises computer means, said computer means being operable to control said means for applying said first electrical signal across said pairs of sensor electrodes and said second electrical signal across said reference electrodes.

11. The system defined in claim 10 further comprising bridge circuit means for measuring the conductance between said adjacent pairs of sensor electrodes when said first electric signal is applied thereacross and for measuring the conductance between said reference electrodes when said second electrical signal is applied thereacross.

12. The system defined in claim 11 wherein said reference electrodes are mounted in the pipe wall of said dielectric pipe section and have their inner end flush with the inner wall thereof, and wherein said sensor electrodes are mounted in axially spaced relation to one another in the wall of said dielectric pipe section and have their inner ends flush with the inner wall thereof said pipe section being connected in a substantially horizontal section of said pipeline with said pair of reference electrodes located at the top of the pipe section.

13. The system defined in claim 12 further comprising a plurality of sets of reference electrodes mounted in said pipe section, said reference electrodes of each said pair being located in axially spaced relation to one another, with the pairs of electrodes being spaced from one another around the periphery of the pipe section, whereby the pipe section may be removed from the pipeline and rotated a predetermined amount and then reinstalled to place a different pair of reference electrodes at the top thereof, with only the set of reference electrodes at the top of the pipe section being connected in the system during operation.

14. The system defined in claim 11 further comprising conduit means connected in said pipeline for diverting a portion of a liquid solids slurry flowing through the pipeline, and wherein said pair of reference sensors are mounted in contact with the liquid phase of slurry diverted through said conduit.

* * * * *